United States Patent [19]

White

[11] 4,055,563
[45] Oct. 25, 1977

[54] CYANO INTERMEDIATES FOR PROSTAGLANDINS

[75] Inventor: David R. White, Kalamazoo, Mich.

[73] Assignee: The Upjohn Company, Kalamazoo, Mich.

[21] Appl. No.: 695,147

[22] Filed: June 11, 1976

Related U.S. Application Data

[62] Division of Ser. No. 566,356, April 9, 1975, Pat. No. 3,974,146.

[51] Int. Cl.² .................. C07C 177/00; C07D 307/77
[52] U.S. Cl. ............................. 542/413; 260/343.3 P
[58] Field of Search ...................... 260/343.3 P, 240 R

[56] References Cited

U.S. PATENT DOCUMENTS

| | | | |
|---|---|---|---|
| 3,873,598 | 3/1975 | Crabbe et al. | 260/343.3 P |
| 3,933,889 | 1/1976 | Magerlein | 260/240 R |

FOREIGN PATENT DOCUMENTS

| | | | |
|---|---|---|---|
| 5,018,460 | 2/1975 | Japan | 260/343.3 P |

Primary Examiner—Natalie Trousoe
Assistant Examiner—Jane T. Fan
Attorney, Agent, or Firm—Morris L. Nielsen

[57] ABSTRACT

Intermediates for preparing prostaglandins, represented by the formula

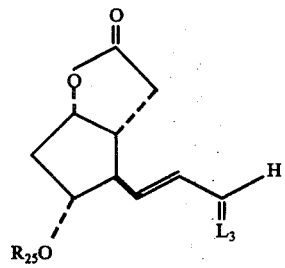

wherein $L_3$ represents

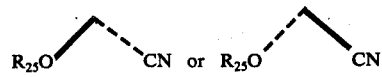

and wherein $R_{25}$ is hydrogen or tetrahydropyranyl or similar group as defined herein. These cyano intermediates are useful intermediates in preparing prostaglandin analogs having pharmacological utility.

5 Claims, No Drawings

CYANO INTERMEDIATES FOR PROSTAGLANDINS

CROSS REFERENCE TO RELATED APPLICATIONS

This application is a division of copending application Ser. No. 566,356 filed Apr. 9, 1975 now issued as U.S. Pat. No. 3,974,146.

BACKGROUND OF THE INVENTION

This invention relates to intermediates useful in the preparation of prostaglandins and to a process for preparing them.

The essential material for this application, including the background of the invention, the disclosure of the invention, and the description of the preferred embodiments, including Preparations and Examples, is incorporated by reference from U.S. Pat. No. 3,974,146, issued to David R. White on Aug. 10, 1976, columns 1-31 inclusive, under the provisions of M.P.E.P. 608.01(p).

SUMMARY OF THE INVENTION

It is the purpose of this invention to provide novel intermediates useful in the preparation of prostaglandins commercially in substantial amount, with high purity, and at reasonable cost. It is a further purpose to provide processes for preparing these intermediates and for utilizing them.

Reference to Charts A and B will make clear the steps by which these processes are performed and by which these compounds are obtained. In these charts, $R_{12}$, $R_{16}$, $R_{21}$, $R_{23}$, s, T, $L_1$, $L_2$, and ~ are defined: $R_{12}$ is

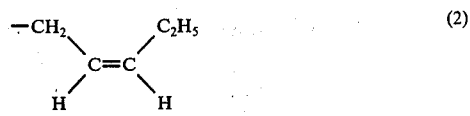

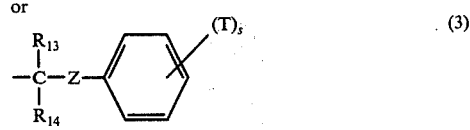

wherein $C_gH_{2g}$ is alkylene of one to 9 carbon atoms, inclusive, with one to 5 carbon atoms, inclusive, in the chain between $-CR_{13}R_{14}-$ and terminal methyl; wherein $R_{13}$ and $R_{14}$ are hydrogen, alkyl of one to 4 carbon atoms, inclusive, or fluoro, being the same or different, with the proviso that $R_{13}$ is fluoro only when $R_{14}$ is hydrogen or fluoro; wherein T is alkyl of one to 4 carbon atoms, inclusive,

CHART A

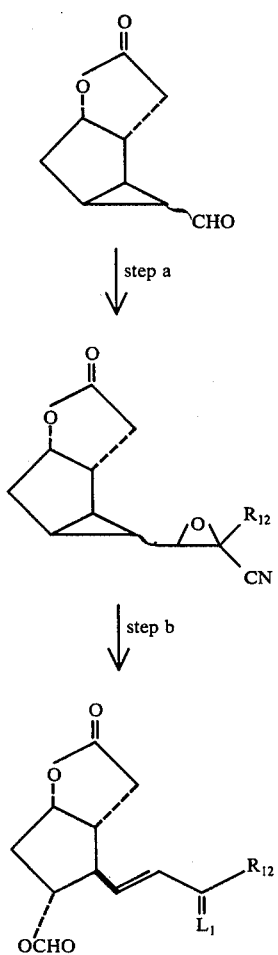

VI

VII

VIII 4,055,563
-continued
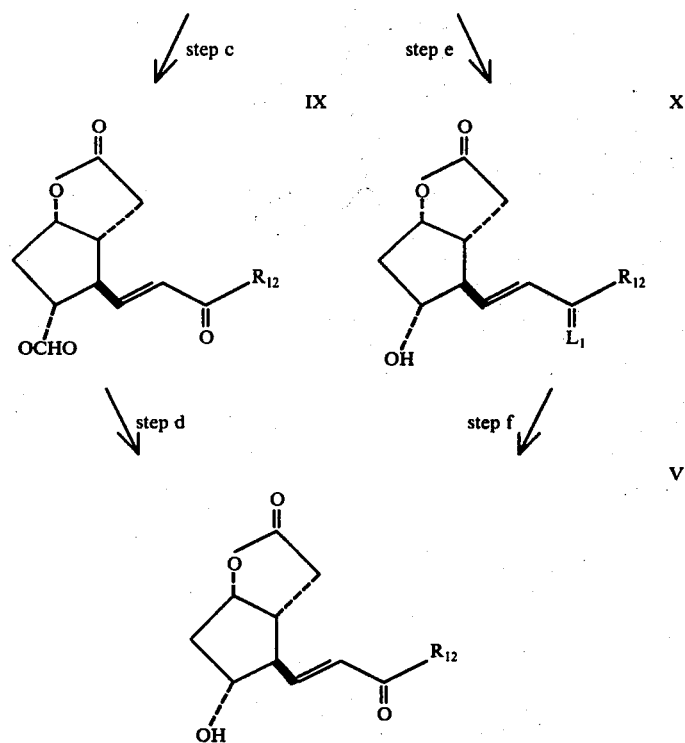
CHART B
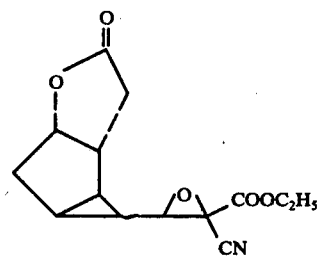
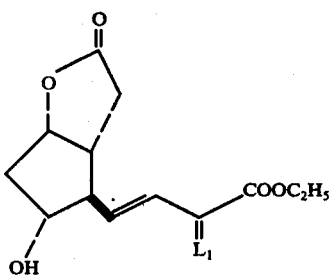

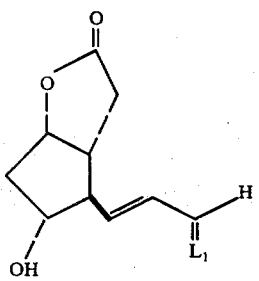

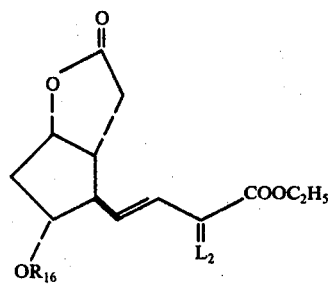

XVII

↓ step L    ↘ step n

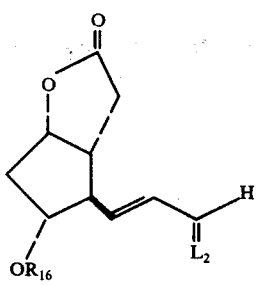

↓ step p

XVIII

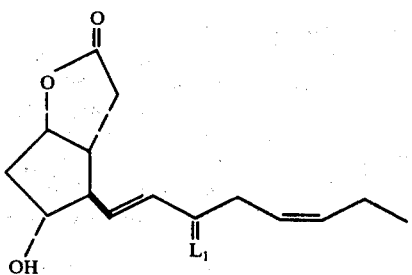

↓ step q

XI

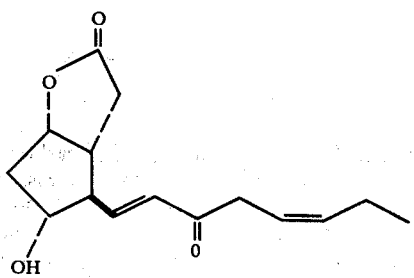

fluoro, chloro, trifluoromethyl, or —OR$_{15}$, wherein R$_{15}$ is hydrogen or alkyl of one to 4 carbon atoms, inclusive, and s is zero, one, 2, or 3, with the proviso that not more than two T's are other than alkyl; and wherein Z represents an oxa atom (—O—) or C$_j$H$_{2j}$, wherein C$_j$H$_{2j}$ is a valence bond or alkylene of one to 9 carbon atoms, inclusive, substituted with zero, one, or 2 fluoro, with one to 6 carbon atoms, inclusive, between —CR$_{13}$R$_{14}$— and the ring; R$_{16}$ is 1-ethoxyethyl, tetrahydropyranyl, tetrahydrofuranyl, or a group of the formula

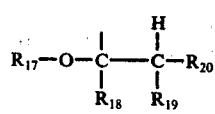

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{18}$ and $R_{19}$ are the same or different, being hydrogen, alkyl of one to 4 carbon atoms, inclusive, phenyl or phenyl substituted with one, 2, or 3 alkyl of one to 4 carbon atoms, inclusive, or, when $R_{18}$ and $R_{19}$ are taken together, —$(CH_2)_a$— or —$(CH_2)_b$—O—$(CH_2)_c$— wherein $a$ is 3, 4, or 5, $b$ is one, 2, or 3, and $c$ is one, 2, or 3 with the proviso that b plus c is 2, 3, or 4, and wherein $R_{20}$ is hydrogen or phenyl; $R_{21}$ is (1) $R_{16}$ as defined above or (2) carboxyacyl —C-(O)$R_{22}$ wherein $R_{22}$ is hydrogen or alkyl of one to 17 carbon atoms, inclusive; $R_{23}$ is hydrogen or alkyl of one to 4 carbon atoms, inclusive; $L_1$ represents

$L_2$ represents

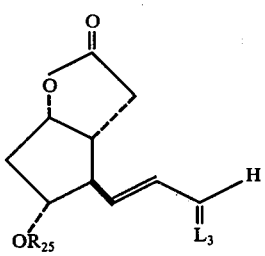

wherein $R_{16}$ is as defined above; and ~ indicates attachment to the cyclopropane ring in endo or exo configuration.

Included in the novel compounds of this invention is an optically active compound of the formula

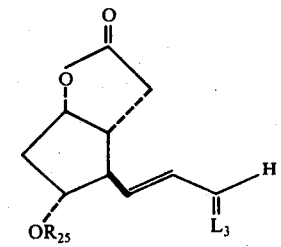

or a mixture of that compound and the enantiomer thereof, wherein $L_3$ represents

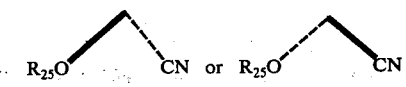

wherein $R_{25}$ is hydrogen or $R_{16}$ as defined above, with the proviso that both $R_{25}$'s are the same; said compound accordingly including compounds XV and XVII of Chart B and no others.

I claim:

1. An optically active compound of the formula

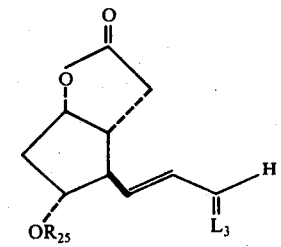

or a mixture of that compound and the enantiomer thereof, wherein $L_3$ represents

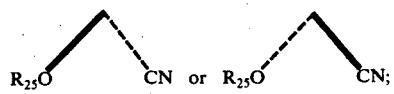

and wherein $R_{25}$ is hydrogen, 1-ethoxyethyl, tetrahydropyranyl, tetrahydrofuranyl, or a group of the formula

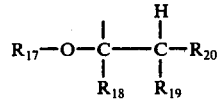

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl or phenyl substituted with one, 2, or 3 alkyl of one to 4 carbon atoms, inclusive, wherein $R_{18}$ and $R_{19}$ are the same or different, being hydrogen, alkyl of one to 4 carbon atoms, inclusive, phenyl or phenyl substituted with one, 2, or 3 alkyl of one to 4 carbon atoms, inclusive, or, when $R_{18}$ and $R_{19}$ are taken together, —$(CH_2)_a$— or —$(CH_2)_b$—O—$(CH_2)_c$— wherein a is 3, 4, or 5, b is one, 2, or 3, and c is one, 2, or 3 with the proviso that b plus c is 2, 3, or 4, and wherein $R_{20}$ is hydrogen or phenyl; with the further proviso that both $R_{25}$'s are the same.

2. An optically active compound according to claim 1.

3. A compound according to claim 1 wherein $R_{25}$ is hydrogen.

4. A compound according to claim 1 wherein $R_{25}$ is 1-ethoxyethyl, tetrahydropyranyl, tetrahydrofuranyl, or a group of the formula

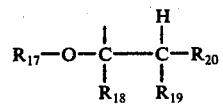

wherein $R_{17}$ is alkyl of one to 17 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{18}$ and $R_{19}$ are the same or different, being hydrogen, alkyl of one to 4 carbon atoms, inclusive, phenyl or phenyl substituted with one, 2, or 3 alkyl of one to 4 carbon atoms inclusive, or, when $R_{18}$ and $R_{19}$ are taken together, —$(CH_2)_a$ — or —$(CH_2)_b$—O—$(CH_2)_c$— wherein $a$ is 3, 4, or 5, $b$ is one, 2, 3, and $c$ is one, 2, or 3 with the proviso that $b$ plus $c$ is 2, 3, or 4, and wherein $R_{20}$ is hydrogen or phenyl.

5. A compound according to claim 4 wherein $R_{25}$ is 1-ethoxyethyl.

* * * * *